United States Patent [19]

Yoshizawa

[11] 4,071,410
[45] Jan. 31, 1978

[54] PROCESS FOR PREPARATION OF PANCREATIC ELASTASE

[75] Inventor: Masayuki Yoshizawa, Kawagoe, Japan

[73] Assignee: Eisai Co., Ltd., Tokyo, Japan

[21] Appl. No.: 738,866

[22] Filed: Nov. 4, 1976

[30] Foreign Application Priority Data

Nov. 8, 1975 Japan .................................. 50-133600

[51] Int. Cl.$^2$ ............................................. C07G 7/026
[52] U.S. Cl. ................................................. 195/66 R
[58] Field of Search ...................... 195/65, 66 R, 114

[56] References Cited

U.S. PATENT DOCUMENTS

| 3,367,836 | 2/1968 | Thuillier | 195/66 R |
| 3,904,479 | 9/1975 | Yoshizawa et al. | 195/66 R |

*Primary Examiner*—Lionel M. Shapiro
*Attorney, Agent, or Firm*—Blanchard, Flynn, Thiel, Boutell & Tanis

[57] ABSTRACT

Pancreatic elastase is prepared by adding the duodenum of a mammalian animal or an extract thereof to a starting material containing a precursor of elastase to thereby activate the elastase precursor and separating the obtained pancreatic elastase.

3 Claims, No Drawings

PROCESS FOR PREPARATION OF PANCREATIC ELASTASE

BACKGROUND OF INVENTION

1. Field of Invention

The present invention relates to a process for preparing pancreatic elastase in a high yield.

In the pancreas of a mammalian animal, elastase is present in the form of a precursor of elastase. Accordingly, in general, elastase is obtained from the pancreas by activating this elastase precursor to convert it to elastase and purifying the activated product.

2. Description of Prior Arts

As the conventional process for the preparation of pancreatic elastase, there are known various processes, for example, the process disclosed in Japanese Patent Publication No. 21557/75 and the Lewis process [The Journal of Biological Chemistry, 222, page 705 (1956)]. In all of these conventional processes, finely cut fresh pancreas which has been activated by autolysis under heating or a dry product of such activated pancreas commercially available as "pancreatin" is used as the starting material. In these known processes, however, activation of the elastase precursor is not sufficiently performed and hence, the yield of elastase is not good.

SUMMARY OF INVENTION

As a result of my research works with a view to developing a process for preparing pancreatic elastase in a high yield, it has been found that when the duodenum of a mammalian animal or an extract thereof is added to a starting material containing a precursor of elastase, activation is performed sufficiently and pancreatic elastase is obtained in a high yield. I have now completed the present invention based on this finding.

In accordance with the present invention, there is provided a process for the preparation of pancreatic elastase characterized by adding the duodenum of a mammalian animal or an extract thereof to a starting material containing a precursor of elastase to thereby activate the elastase precursor. Steps subsequent to the activation step are conducted in the same manner as in the conventional processes, and pancreatic elastase can be obtained in a high yield.

Since all the fresh pancreases of mammalian animals contain elastase precursor irrespective of the kinds of animals, the pancreas of any mammalian animal can be used as the starting material in the present invention. In view of the content of the elastase precursor, fresh pancreas of a pig is most preferred.

Any of starting materials containing an elastase precursor, such as fresh pancreas, residues left after recovery of insulin and kallikrein from fresh pancreas and defatted pancreas, can be used in the present invention. It is especially preferred to use finely cut fresh pancreas as the starting material.

The duodenum of any mammalian animal can be used in the present invention. However, in order to prevent incorporation of minute amounts of different kinds of elastases, it is preferred to use the duodenum of the same kind of an animal as that of the animal from which the starting pancreas has been collected. The duodenum may be added in the state where it is finely cut. It is also possible to use an extract obtained by extracting the fresh duodenum with an aqueous solvent such as an acidic or weakly alkaline aqueous solution, an aqueous solution of a salt, a buffer solution or the like. The object of the present invention can be sufficiently attained when the duodenum is added in an amount of 0.5 to 20% by weight based on the fresh pancreas. When an extract of the duodenum is used, it is added in an amount corresponding to the above-mentioned amount of the fresh duodenum.

Activation is accomplished by adding the duodenum or an extract thereof to the elastase precursor-containing starting material and allowing the mixture to stand for a certain period of time. Good results are obtained when the activation is carried out in the presence of an aqueous medium such as a weakly acidic or alkaline aqueous solution, an aqueous solution of a salt, a buffer solution or the like. When the water content is high in the starting material, an aqueous medium need not be added. The activation is conducted at a pH of from about 4 to about 10, preferably at a pH of from 6 to 9. If the pH is lower than 4 or higher than 10, the stability of elastase is bad, and hence, it is not practically preferred to conduct the activation at such a pH. The activation is hardly influenced by the temperature if the activation temperature is 5° to 40° C. Formation of elastase arrives at a maximum level in about 2 hours. When the mixture is further allowed to stand, other substances contained in the starting material undergoes autolysis and the subsequent separation and purification of the resulting elastase can be facilitated. Accordingly, it is preferred to allow the mixture for a long time even after completion of the activation.

After the above-mentioned activation according to the present invention, elastase can be separated and purified according to known methods such as salting-out, dialyzing and crystallizing methods.

When fresh pig pancreas is activated according to the process of the present invention, the elastase content is increased to about 0.45%, while the elastase content is only about 0.09% if the activation is carried out according to the known process. In short, the activation ratio attained in the present invention is about 5 times as high as the activation ratio attained in the conventional process. According to the process disclosed in Japanese Patent Publication No. 21557/75, which provides a highest yield of elastase among the known processes, when fresh pig pancreas or pig pancreatin is used as the starting material, the yield is about 0.9 g/Kg or about 6 g/Kg (about 1 g/Kg of fresh pancreas), respectively. When elastase is prepared from fresh pig pancreas according to the process of the present invention, the yield is about 2.7 or about 2.8 g/Kg. Accordingly, the yield attained in the present invention is about 3 times as high as the yield attainable in the above known process. Moreover, if fresh pancreas or the like is activated according to the process of the present invention, the elastase fraction can easily be separated from the kallikrein fraction at the subsequent salting-out step. Accordingly, kallikrein can also be prepared as a by-product in the process of the present invention.

As will be apparent from the foregoing illustration, the process of the present invention is a very industrially excellent process for the preparation of pancreatic elastase.

The present invention will now be described in detail by reference to the following examples and experiments, in which the elastase activity was measured according to a modification of the method of K. C. Robbins et al. [Arch. Blochem. Biophys., 66, page 396 (1957)]. More specifically, the enzymatic activity of releasing 1 μg of tyroine from elastin for 1 minute when elastase is reacted with elastin at 37° C under shaking in Paliztish buffer solution is designated as 1 unit.

EXAMPLE 1

One Kg of fresh pig pancreas and 100 g of pig duodenum were minced, and 1 l of distilled water was added to the minced mixture. The mixture was blended under agitation in a homogenizing mixer, and 2N sodium hydroxide was added to the mixture to adjust the pH to 7 to 7.5. The mixture was allowed to stand at 10° C. for 16 hours to effect activation. Then, 2 l of a 0.2M acetate buffer solution (having a pH of 4.8) was added and the mixture was agitated for 4 hours and allowed to stand overnight. Then, 300 g of Celite was added to the mixture, and resulting mixture was agitated and filtered.

Solid ammonium sulfate was added to the filtrate to 45% saturation, whereby salting-out was carried out. The resulting precipitate was dissolved in 0.1M phosphate buffer solution (pH: 7.0) in such an amount as 6 ml per 1 g of the precipitate. The solution was allowed to stand in an incubator at 20° C. for 20 hours. The solution was clarified and filtered, and the filtrate was cooled to 4° C. and ammonium sulfate was added to the filtrate to 35 % saturation. The precipitate was collected by filtration, and it was then dissolved in an amount, such as 6 ml per 1 g of the precipitate, of 0.1M carbonate buffer solution (having a pH of 7.0). Then, seed crystals of elastase were added to the solution and the mixture was agitated at 5° C. to precipitate crystals. The yield of the elastase crystals was 2.7 g and the elastase activity was 155 units per mg.

For comparison, elastase was prepared according to the known process. More specifically, 1 Kg of fresh pig pancreas was minced and was allowed to stand at 30° C. for 8 hours to effect activation. Then, 3 l of 0.1M acetate buffer solution (having a pH of 4.5) was added and the mixture was agitated for 4 hours and allowed to stand overnight. Then, 300 g of Celite was added to the mixture and the resulting mixture was agitated and filtered. The resulting filtrate was subjected to the salting-out and subsequent post treatments in the same manner as described above. The yield of elastase crystals was 0.9 g and the elastase activity was 150 units per mg.

As will be apparent from these results, according to the present invention it is possible to obtain elastase in a yield 3 times as high as the yield attainable in the conventional process.

EXAMPLE 2

100 g of pig duodenum was minced and 400 ml of 0.1N acetic acid was added thereto. The mixture was agitated for 30 minutes to effect extraction. Then, 40 g of Celite was added to the mixture, and the resulting mixture was filtered to obtain a duodenum extract.

One Kg of fresh pig pancreas was minced and 3 l of a 0.1M sodium acetate solution was added thereto. Then, the above duodenum extract was added to the liquid mixture and the pH was adjusted to 7 to 7.5 by addition of 2N sodium hydroxide solution. The mixture was allowed to stand at 10° C. for 16 hours to effect activation. Then, 90 ml of 2N acetic acid was added to the resulting liquid and the mixture was agitated for 4 hours and allowed to stand overnight. Then, 300 g of Celite was added to the mixture and the resulting mixture was agitated and filtered. Solid ammonium sulfate was added to the filtrate to 45 % saturation, whereby salting-out was conducted. The resulting precipitate was dissolved in 0.1M phosphate buffer solution (having a pH of 7.0) in such an amount as 6 ml per 1 g of the precipitate. The solution was allowed to stand in an incubator at 20° C. for 20 hours. The solution was filtered, and the filtrate was cooled to 4° C. and ammonium sulfate was added to the filtrate to 35 % saturation. The precipitate was obtained by filtration and dissolved in 0.1M carbonate buffer solution (having a pH of 7.0) in such an amount as 6 ml of 1 g of the precipitate. Seed crystals of elastase were added to the solution and the solution was agitated at 5° C. to precipitate crystals. The yield of elastase crystals was 2.8 g and the elastase activity was 160 units per mg.

EXPERIMENT 1

To 1 Kg of minced fresh pig pancreas were added 1 l of water and 100 g of minced pig duodenum, and the mixture was allowed to stand at 10° or 30° C. The elastase content in the fresh pancreas was examined at prescribed intervals. For comparison, the above experiment was conducted at 30° C. in the same manner as above except that duodenum was not added. The elastase content was determined by measuring the elastase activity according to a modification of Shotton's method [Methods in Enzymology, 19, pages 113 to 140] using N-benzoyl-L-alanine methyl ester as a substrate and comparing the thus measured activity with the activity of pure elastase to calculate the elastase content. Results are shown in the following Table.

Table

| | Elastase Content (%) in Fresh Pancreas | | | |
| --- | --- | --- | --- | --- |
| | 30 minutes | 2.5 hours | 10 hours | 20 hours |
| 10 % of duodenum added, 10° C. | 0.40 | 0.45 | 0.45 | 0.45 |
| 10 % of duodenum added, 30° C. | 0.40 | 0.44 | 0.44 | 0.44 |
| duodenum not added, 30° C. (comparison) | 0.02 | 0.05 | 0.09 | 0.09 |

As will be apparent from the above results, when the duodenum is added to fresh pancreas, the maximum elastase content is about 5 times as high as the maximum elastase content attained when no duodenum is added, and the activation is sufficiently advanced when the duodenum is added.

The embodiments of the invention in which an exclusive property or privilege is claimed are defined as follows:

1. A process for preparing pancreatic elastase, which comprises adding the duodenum of a mammalian animal or an extract thereof to pancreatic material containing a precursor of elastase to thereby activate the elastase precursor and separating pancreatic elastase.

2. A process as claimed in claim 1, in which said starting material is the fresh pancreas of a pig.

3. A process as claimed in claim 2, in which there is used the duodenum of the same kind of an animal as that of the animal from which the starting pancreas has been collected.

* * * * *